United States Patent [19]

Midcalf

[11] Patent Number: 4,769,037
[45] Date of Patent: Sep. 6, 1988

[54] ARTIFICIAL REPLACEMENT KIDNEY IMPLANT AND METHOD OF DIALYZING BLOOD

[76] Inventor: Robert J. Midcalf, 120 W. Perkins, Merrill, Mich. 48637

[21] Appl. No.: 924,059

[22] Filed: Oct. 28, 1986

[51] Int. Cl.$^4$ .................. A61F 2/04; A61M 37/00
[52] U.S. Cl. ................................. 623/12; 604/5; 623/66
[58] Field of Search .............. 623/11, 12, 66; 604/5, 604/29; 128/DIG. 3

[56] References Cited

U.S. PATENT DOCUMENTS

| | | | |
|---|---|---|---|
| 3,505,686 | 4/1970 | Bodell | 623/66 |
| 4,127,481 | 11/1978 | Malchesky et al. | 604/5 X |
| 4,354,933 | 10/1982 | Lester | 604/5 |

FOREIGN PATENT DOCUMENTS 2054446 10/1972 Fed. Rep. of Germany ........ 623/12
2558363 7/1977 Fed. Rep. of Germany ........ 604/5

Primary Examiner—Ronald L. Frinks
Attorney, Agent, or Firm—John J. Swartz

[57] ABSTRACT

An artifical replacement kidney implant for dializing blood within a human body comprising at least one blood panel having an inlet for coupling to the artery of a body and an outlet for coupling to the vein of a body to receive blood to be dialized and to discharge dialized blood respectively. The blood panel includes a semipermeable membrane through which biologically active material contained within the body of blood diffuses.

An absorbent panel is disposed at the opposite side of the membrane for passing the biologically active material and mechanism is provided for communicating the biologically active material to the ureter of the body.

One aspect of the invention also includes the insitu process of dializing body blood.

16 Claims, 2 Drawing Sheets

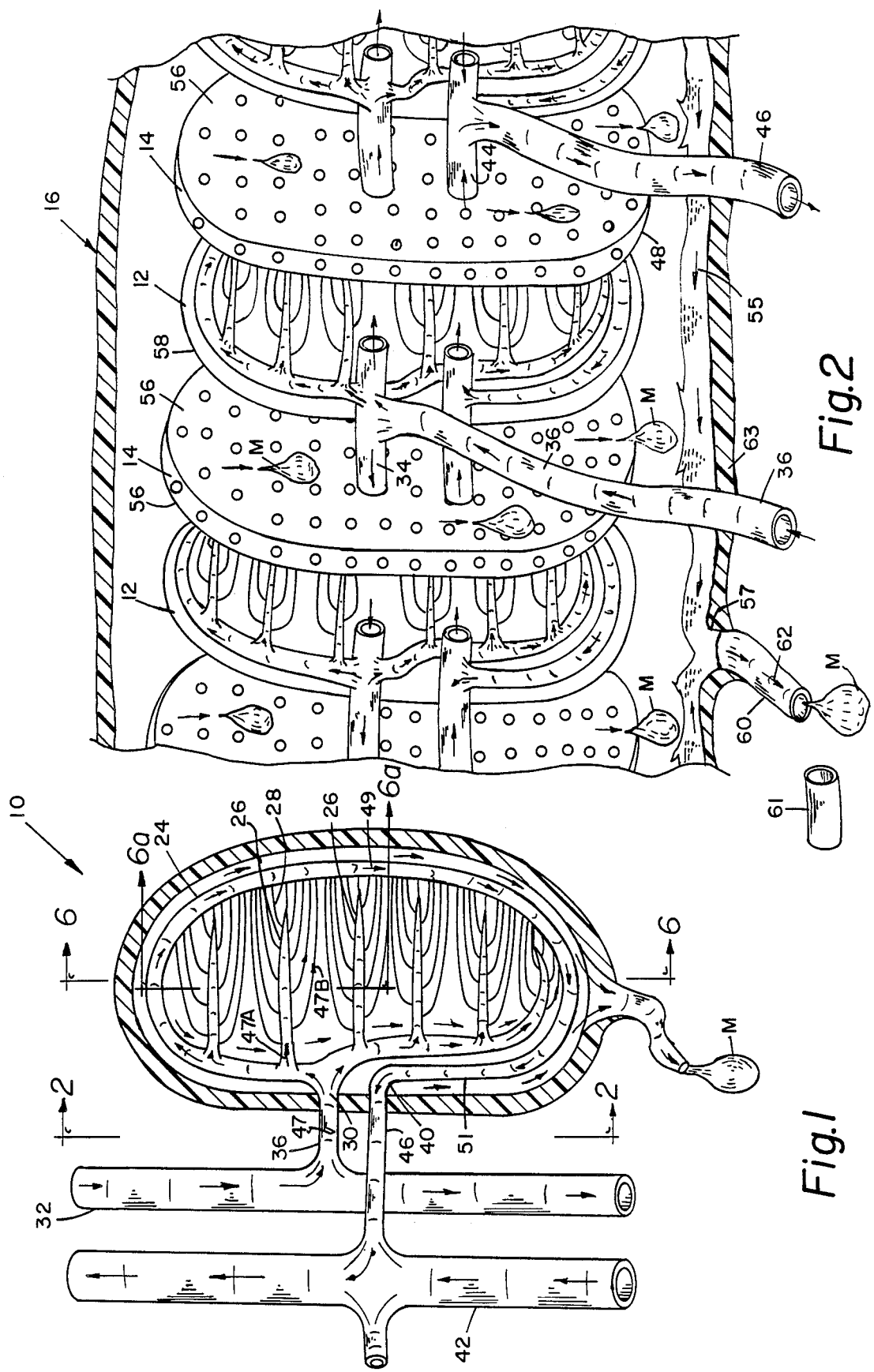

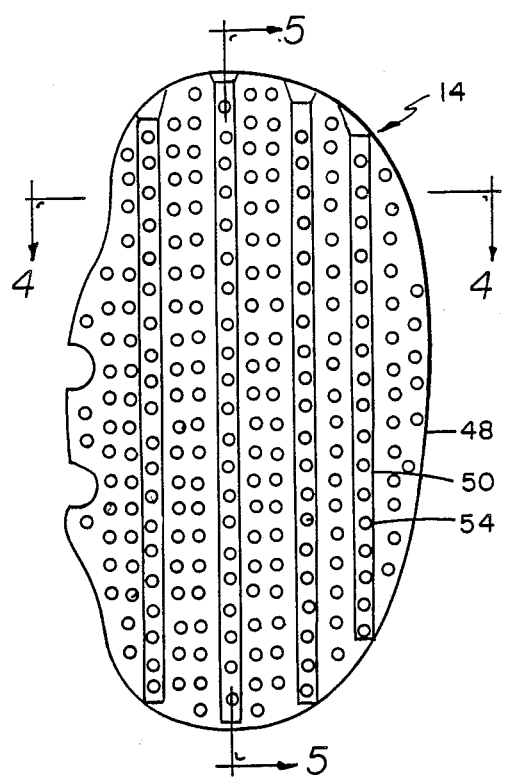
Fig.3
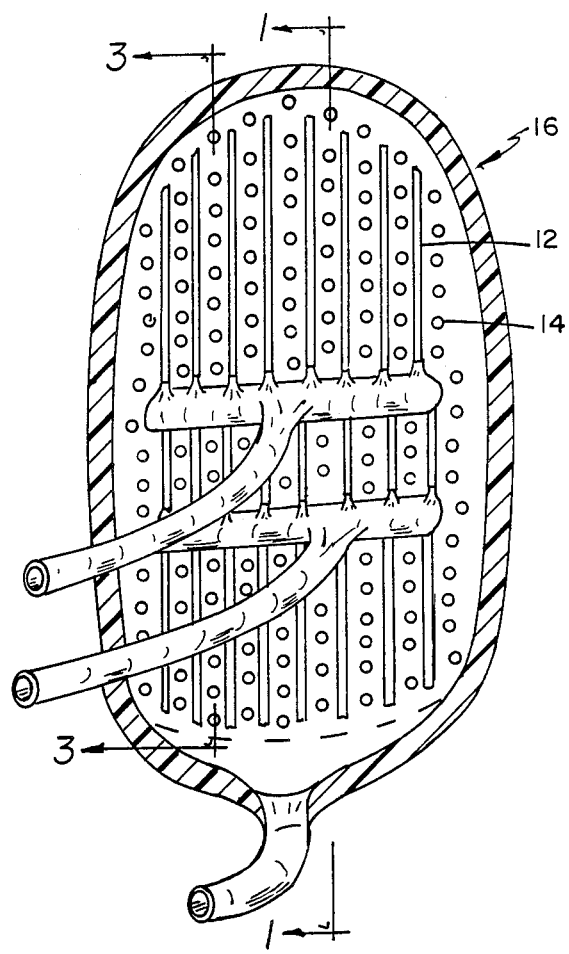
Fig.6
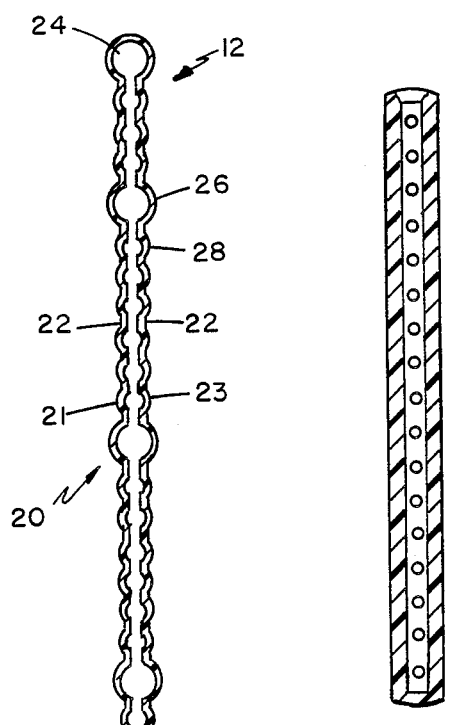
Fig.6a
Fig.5
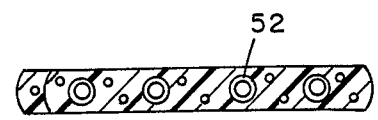
Fig.4

ARTIFICIAL REPLACEMENT KIDNEY IMPLANT AND METHOD OF DIALYZING BLOOD

BACKGROUND OF THE INVENTION

1. FIELD OF THE INVENTION

This invention relates to apparatus for, and a method of, dialyzing blood and, more particularly, to an artificial replacement kidney which is implanted in a human body and includes a non-liquid, absorbent member for receiving and passing biologically active material, which is removed from the blood to the body ureter.

2. DESCRIPTION OF RELATED ART

When an individual's biological kidney malfunctions, the individual's blood becomes contaminated with excess biologically active material such as, for example, toxicants, metabolites, nutrients, and/or medicaments. Heretofore, there have been two basic approaches to removing such biologically active material.

One such approach has been a hemo-dialysis machine to which the user is periodically "hooked-up". With the use of a hemo-dialysis machine, the blood to be dialyzed is withdrawn from an individual's artery and passed over one side of a semi-permeable membrane which allows the biologically active material to pass therethrough without allowing the blood to pass. On the opposite side of the membrane, a dialyzing fluid is provided for carrying away the biologically active material to a remote location where it is filtered. Such a prior art device is illustrated in U.S. Pat. No. 3,489,647 issued to T. Kolobow on Jan. 13, 1970. This concept was also alluded to in an article entitled *The Model and Simulation of A New Artificial Kidney*, published in the *Proceedings of the 23rd Annual Conference on Engineering in Medicine and Biology*, Washington, DC, U.S.A., on or about Nov. 10, 1970 by Reuben G. Carbonell, Edward F. Leonard and Louis Theodore.

In an Aug. 10, 1967 edition of the *Washington Post*, a *Washington Post* staff writer, Nate Hastltine, discussed an artificial kidney which could be installed within the body, but it included a foot long cylinder of hollow fiber tubes and also utilized a dialyzing fluid which was introduced to the device and removed from it by outside the body techniques.

The second basic prior art approach to dialyzing human blood, is sometimes referred to as the peritoneal method which disposes a quantity of dialyzing fluid, such as 0.5 percent dextrose solution, within the individual's abdominal cavity. The serous membrane, which lines the cavity of the individual's abdomen, functions as a dialyzing membrane which allows the biologically active material embedded in the blood stream to pass inwardly through the serous membrane to the dialyzing fluid. This fluid must be withdrawn and replaced several times a day and requires a catheter to be coupled to the abdomen. The peritoneal method functions 24 hours a day, however, the dialyzing fluid must be withdrawn several times a day whereas a hemo-dialysis machine is intermittently operated. For example, a hemo-dialysis machine may be operated six hours every day and a half to two days. Older individuals frequently cannot utilize the peritoneal approach because they are not physically able to withstand the surgical operation required to insert the catheter which is utilized to extract and insert the dialyzing fluid to the abdomen.

The prior art devices which have been used heretofore truly are not true artificial organs in that they are not implanted in the body and require continuous maintenance and the dialyzing fluid must be continually carried away from the body.

Accordingly, it is an object of the present invention to provide a new and novel hemo-dialysis machine and method which will be substantially less expensive and time consuming than have been the prior art hemo-dialysis machines.

Another object of the present invention is to provide a method and apparatus for extracting biologically active material from human blood and which can be implanted in the body.

Yet another object of the present invention is to provide an artificial kidney which can be permanently implanted in a body and which can function without outside the body resources and/or dialyzing fluid.

Another object of the present invention is to provide a new and novel hemo-dialysis machine of the type described which is substantially reduced in size compared to the hemo-dialysis machine utilized heretofore.

It is a further object of the present invention to provide a hemo-dialysis machine which does not require a dialyzing fluid.

It is still another object of the present invention to provide a dialysis machine which does not include a dialyzing fluid which is pumped away from the body.

It is another object of the present invention to provide a dialysis machine and method which utilizes a non-liquid material for receiving the biologically active material extracted from the user's bloodstream.

It is another object of the present invention to provide an artificial replacement kidney implant which utilizes sponge material for carrying away the biologically active material to the body ureter.

Yet another object of the present invention is to provide an artificial replacement kidney implant which utilizes an absorbent material having a plurality of drain tubes therein for carrying away the biologically active material.

It is yet another object of the present invention to provide an artificial replacement kidney implant which implant of the type described which communicates the biologically active material extracted from the blood to the ureter of the human body.

Other objects and advantages of the present invention will become apparent to those of ordinary skill in the art as the description thereof proceeds.

SUMMARY OF THE INVENTION

An artificial replacement kidney implant for dialyzing body blood within a human body comprising: a chamber having an inlet for receiving blood to be dialyzed and an outlet for discharging dialyzed blood; mechanism for coupling the inlet to a human artery within said body; mechanism for coupling said outlet to a human vein within said body to communicate the dialyzed blood to the vein; the chamber including a semi-permeable membrane through which biologically active material in the blood to be dialyzed diffuses from one side to the opposite side; non-liquid mechanism abutting the opposite side of the membrane for receiving and passing the biologically active material; and mechanism communicating the biologically active material from the non-liquid mechanism to the body ureter.

BRIEF DESCRIPTION OF THE DRAWINGS

The invention may be more readily understood by referring to the accompanying drawings, in which:

FIG. 1 is a sectional end elevational view taken along the line 1—1 of FIG. 6;

FIG. 2 is a front, side exploded view, taken along the line 2—2 of FIG. 1; parts of an outer silicone encasement, which encapulates a plurality of interspersed blood panels and waste discharge panels, being broken away to more particularly illustrate the underlying blood panels and waste discharge panels;

FIG. 3 is a sectional side elevational view taken along the line 3—3 of FIG. 6, illustrating one waste discharge panel only;

FIG. 4 is a top plan sectional view of the waste discharge panel only, taken along the line 4—4 of FIG. 3;

FIG. 5 is a front sectional side view of a waste discharge panel only, taken along the line 5—5 of FIG. 3;

FIG. 6 is a sectional front view, taken along the line 6—6 of FIG. 1; and

FIG. 6a is a greatly enlarged sectional front elevational view, taken along the line 6a—6a of FIG. 1 illustrating the upper half of one blood panel only.

DESCRIPTION OF THE PREFERRED EMBODIMENT

An artificial replacement kidney implant constructed according to the present invention, generally designated 10, includes a plurality of blood panels, generally designated 12, alternately laterally interspersed with a plurality of waste discharge panels, generally designated 14, disposed therebetween. The blood panels 12 and waste discharge panels 14 are encased within a silicone envelope, or encasement, generally designated 16.

Each of the blood panels 12 includes an inlet 30 which is coupled to a renal artery 32 within a person's body via a manifold tube 34 and a flexible conduit 36. The opposite discharge end or outlet 40 of the blood panel 12 is coupled to a renal vein 42 within the body via a discharge manifold 44 and a flexible conduit 46. The manifolds or connectors 44 and conduits 36 and 46 may suitably comprise silicone rubber. The progressive passage of the blood through the blood panels 12 is schematically represented by the arrows 47, 49 and 51.

More particularly, each blood panel includes a generally hollow, semi-permeable membrane, generally designated 20, comprising a pair of cellophane sheets 21 and 23 sandwiched together but spaced apart at selected locations to provide a plurality of vertically spaced main channel members 26 and a plurality of lesser diameter feeder channel members 28 in fluid communication with a circumferentially extending channel 24 coupled, at opposite ends to the inlet 30 and outlet 40. The breadth or thickness of the red blood cells per se is approximately 1/6 greater than the breadth or thickness of the minute holes, passages or openings (not shown) in the cellophane membrane 20 and thus the normal blood cells cannot pass outwardly through the membrane 20, whereas the biologically active material can diffuse through the holes in the cellophane membrane 20 and will collect on the opposite or outside surface 22 of the membrane 20. The molecules of the biologically active material are smaller than the molecules of the blood and thus are able to diffuse through the cellophane membrane, to collect on the outer blood panel surface 58 as represented by the droplets M. It is to be understood, of course, that the membrane material may suitably comprise other material such as silicone rubber, regenerated cellulose, polyethylene and latex.

Each of the waste discharge panels 14 comprises a layer 48 of open cellular and/or porous material, such as sponge, having a plurality of vertical passages 50 therethrough which receive a plurality of hollow conduits 52 each having a plurality of lateral openings 54 in the side walls thereof. The laterally outer sides 56 of the sponge layers 48 abut the laterally outer sides 58 of the adjacent blood panels 12 and absorb the biologically active material represented by the droplets M. The tubes 52 will in effect act as drain tile for draining or siphoning the biologically active material M away from the blood panels 12.

The device can typically include eight blood vessel panels 12 supported by nine synthetic sponge panels 14.

The envelope 16 may suitably comprise a jacket or encasement made of silicone rubber of the like to hold the blood panels 12 and sponge panels 14 in the contiguous side by side relationship, as illustrated, and to receive the biologically active material M along the bottom portion thereof as illustrated at 55. The blood panels 12 are flaccid and thus the sponge panels 14 provide lateral support for the blood panels 12.

The bottom wall 63 of the encasement jacket 16 includes a port 57 which is coupled to the ureter, schematically designated 61 of a human body, via a hollow tube 60 so that the biologically active material M is passed through the port 57 and tube 60 to the human bladder in the direction of the arrow 62.

THE OPERATION

The artificial replacement kidney implant 10 is surgically implanted into the body cavity as a replacement for the biological kidney. The blood panels 12 are surgically coupled to the user's artery 32 via tubes 36 and the user's veins 42 are surgically coupled to the blood panel discharge ports 40 for discharging dialyzed blood via tubes 46.

The ureter of the human is surgically coupled to the jacket 16 to receive the waste products M via a tube 60 so that the waste products are carried to the bladder of the individual in which the kidney is implanted. The blood will flow to the inside of the blood panels 12 in the direction of the arrows 47, 47A, and 47B and thence back to the vein in the direction illustrated by the arrows 49 and 51 after it has been dialyzed. The biologically active material will pass laterally outwardly through the membrane 20 and be collected on the outer blood panel surface 58 via the sponge material 48. The biologically active material M will pass through the panel surface 58 to drain tubes 52, to the bottom wall 63 of the encasement 16, and thence through the drain tubes 62 to the body ureter 61.

The apparatus 10 will provide a continual, 24 hours per day, in situ dialyzing function within the body and does not require a dialyzing fluid to be introduced to and/or extracted from the body and/or the machine.

it is to be understood that the drawings and descriptive matter are in all cases to be interpreted as merely illustrative of the principles of the invention, rather than as limiting the same in any way, since it is contemplated that various changes may be made in various elements to achieve like results without departing from the spirit of the invention or the scope of the appended claims.

What I claim is:

1. An artificial replacement kidney implant for insitu removing biologically active material from body blood comprising:
   at least one hollow blood receiving panel having an inlet for receiving blood to be dialyzed and an outlet for discharging dialyzed blood;
   means for coupling said inlet to a body artery;
   means for coupling said outlet to a body vein;
   said panel comprising a semi-permeable membrane through which biologically active material in the blood diffuses; and
   waste discharge means abutting said membrane for receiving and passing said biologically active material, which has diffused through said membrane, to the body ureter;
   said waste discharge means comprising porous means and at least one drain tube embedded therein for receiving and passing said biologically active material.

2. The artificial kidney set forth in claim 1 wherein said porous means comprises a sponge.

3. An artificial replacement kidney implant for dialyzing body blood within a human body comprising:
   a chamber having an inlet for receiving blood to be dialyzed and an outlet for discharging dialyzed blood;
   means for coupling said inlet to a human artery within said body;
   means for coupling said outlet to a human vein within said body;
   said chamber including a semi-permeable membrane through which biologically active material in said blood to be dialyzed diffuses;
   non-liquid means abutting said membrane for receiving and passing said biologically active material which has diffused through said membrane; and
   means for communicating said biologically active material from said non-liquid means to a ureter within said body;
   said non-liquid means comprising
     absorbent means for absorbing said biologically active material; and
     at least one hollow drain tube embedded in said absorbent means.

4. An artificial kidney for removing biologically active material from body blood comprising:
   a hollow panel having a blood receiving inlet and a blood discharging outlet;
   said panel including a membrane through which said biologically active material passes but which prevents the passage of said blood;
   non-liquid absorbent means including a sponge adjacent said membrane for receiving and passing said biologically active material; and
   drain means for draining said biologically active material from said non-liquid absorbent means including at least one drain tube embedded in said absorbent means.

5. The artificial kidney set forth in claim 4 wherein said absorbent means comprises a sponge panel.

6. An artificial kidney for removing biologically active material from body blood comprising:
   a hollow panel having a blood receiving inlet and a blood discharging outlet;
   said panel including a membrane through which said biologically active material passes but which prevents the passage of said blood; and
   non-liquid absorbent means including a sponge panel adjacent said membrane and a plurality of drain tubes embedded in said panel for receiving and passing said biologically active material.

7. The artificial kidney set forth in claim 6 wherein said non-liquid absorbent means including waste discharge means and means for coupling said waste discharge means to a body ureter.

8. The artificial kidney set forth in claim 6 including means for coupling said inlet to a body artery and means for coupling said outlet to a body vein.

9. An artificial replacement kidney implant for dialyzing body blood within a human body without the necessity of any mechanism external to the body comprising:
   a chamber having an inlet for receiving blood to be dialyzed and an outlet for discharging dialyzed blood;
   means for coupling said inlet to a human artery within said body;
   means for coupling said outlet to a human vein within said body;
   said chamber including a semi-permeable membrane through which biologically active material in said blood to be dialyzed diffuses;
   non-liquid absorbent means abutting said membrane for receiving and passing said biologically active material which has diffused through said membrane; and
   means for communicating said biologically active material from said non-liquid absorbent means to a body waste discharge system such as a ureter within said body.

10. The artificial kidney implant set forth in claim 9 wherein said non-liquid means comprises a sponge panel.

11. The artificial kidney implant set forth in claim 9 wherein said non-liquid means includes at least one hollow drain tube embedded in said absorbent means.

12. The artificial kidney implant set forth in claim 11 wherein said drain tube includes a side wall having a plurality of spaced apart openings therein.

13. An artificial replacement kidney implant for dialyzing body blood within a human body cavity comprising:
   a plurality of hollow blood receiving panels each having an inlet for receiving blood to be dialyzed and an outlet for discharging dialyzed blood;
   each of said panels including a semi-permeable flaccid membrane through which any biologically active material within said blood diffuses;
   a plurality of porous non-liquid absorbent means interspersed between said panels to provide lateral support for said panels and abutting said membranes for absorbing and passing said biologically active material;
   envelope means for enveloping said panels and said absorbent means to maintain said panels and said absorbent means in contiguous relation and to receive said biologically active material from said absorbent means;
   means, passing through said envelope means, for coupling said inlets to a human artery within said body to communicate blood to be dialyzed to said blood receiving panels;
   means, passing through said envelope means, for coupling said outlets to a human vein within said body to communicate dialyzed blood to a human vein within said body;

said envelope means including a discharge port for discharging said biologically active material; and means for coupling said discharge port to a ureter within said body for communicating said biologically active material to a human bladder within said body.

14. An in situ process of dialyzing blood within the body without utilizing any mechanism external to the body comprising:

communicating blood to be dialyzed from a body artery to one side of a semi-permeable membrane through which biologically active material, included with the blood, diffuses and communicating the dialyzed blood to a body vein; and collecting the biologically active material with non-liquid absorbent means abutting the opposite side of said membrane and communicating said biologically active material to a body ureter without utilizing any mechanism external to the body.

15. The process set forth in claim 14 wherein said step of collecting the biologically active material comprises absorbing the biologically active material and passing said material through a plurality of drain tubes.

16. The process set forth in claim 14 wherein said step of communicating blood comprises surgically coupling the inlet of a hollow blood receiving panel to a body artery and surgically coupling the outlet of said blood receiving panel to a body vein; and the step of collecting the biological material includes the step of surgically coupling said non-liquid absorbent means to the body ureter.

* * * * *